United States Patent [19]
Honigs et al.

[11] Patent Number: 5,545,376
[45] Date of Patent: Aug. 13, 1996

[54] DRYING METHOD AND APPARATUS FOR INFRARED ANALYSIS OF AQUEOUS SAMPLES

[75] Inventors: David E. Honigs, Laurel; Donald Lynch, Germantown, both of Md.

[73] Assignee: Perstorp Analytical, Inc., Silver Spring, Md.

[21] Appl. No.: 561,418

[22] Filed: Aug. 1, 1990

[51] Int. Cl.$^6$ .............................. B01L 9/00; F26B 19/00
[52] U.S. Cl. ........................ 422/104; 422/99; 422/101; 422/124; 34/202; 34/218; 34/224
[58] Field of Search .............................. 250/304; 350/36, 350/38; 34/202, 218, 224; 392/460; 219/401, 405, 411; 436/171, 167, 177, 178, 181, 902; 210/445; 422/101, 99, 104, 124; 55/503, 511

[56] References Cited

U.S. PATENT DOCUMENTS

| | | | |
|---|---|---|---|
| 1,888,150 | 11/1932 | Walker | 55/503 X |
| 2,127,397 | 8/1938 | Freedlander | 55/503 X |
| 3,487,624 | 1/1970 | Tignanelli | 55/511 X |
| 3,530,292 | 9/1970 | Hill | 250/304 |
| 3,919,089 | 11/1975 | Gonzalez | 210/445 |
| 3,999,304 | 12/1976 | Doty | 55/511 X |
| 4,301,010 | 11/1981 | Eddleman et al. | 422/101 X |
| 4,362,047 | 12/1982 | vonReis et al. | 55/503 X |
| 4,377,641 | 3/1983 | Dee et al. | 436/162 X |
| 4,841,145 | 6/1989 | Wada et al. | 250/304 |
| 4,942,297 | 7/1990 | Johnson et al. | 250/304 |

*Primary Examiner*—Arlen Soderquist
*Attorney, Agent, or Firm*—Lane, Aitken & McCann

[57] ABSTRACT

In the system for analyzing aqueous samples, the aqueous sample is deposited upon a sheet of filter paper which is held in a filter holder by clamping the peripheral edges of the filter paper between male and female threaded members of the filter holder. The filter paper with the sample is dried by a heated air stream directed perpendicularly toward the paper so that it flows around and through the paper. After the sample has been dried, it is analyzed by near infrared spectral analysis to measure the constituents of the dried sample.

5 Claims, 2 Drawing Sheets

DRYING METHOD AND APPARATUS FOR INFRARED ANALYSIS OF AQUEOUS SAMPLES

This invention relates to the quantitative analysis of liquid in which a liquid sample is dried and then subjected to spectral analysis in the near infrared spectrum.

BACKGROUND OF THE INVENTION

In the quantitative analysis of materials by NIR spectroanalysis, a sample material is irradiated with infrared light and the intensity of infrared light reflected by or transmitted through the sample is measured at narrow band wavelengths distributed through the near infrared spectrum. When the sample is a solid dry material, the percentages of the constituents of the sample can be accurately measured by this technique; however, when the sample is a liquid sample, and, in particular, an aqueous liquid sample, the accurate measurement of the constituents of the sample becomes much more difficult because the water in the sample is perhaps the most strongly absorbing and temperature dependent material in the near infrared spectrum. Because of these characteristics, the presence of water in the sample causes background noise, reduces the accuracy of measurements on the sample and significantly reduces the ability of the analysis to detect constituents that are present in small percentages.

To overcome the problem presented by water in aqueous samples, it has been proposed to deposit the liquid sample on a porous base, such as a piece of filter paper and then dry the sample with hot air. The spectroanalysis is then performed on the dried concentrate. However, because of the problems of obtaining uniform drying, it has proved difficult to obtain accurate measurements by this technique.

Professor Marc Meurens has developed a technique in which the filter paper is supported on a wire screen supported in turn on top of a hollow cylindrical column. Heated air is then directed toward the top of the filter containing the deposited sample in a manner to allow the heated air to pass around the filter as well as through the filter so as to dry the sample. The technique achieves relatively uniform drying of the sample deposited in the filter and achieves measurements of the constituents of the original liquid sample which are accurate within about one percent. While this accuracy is satisfactory for many applications, a higher degree of accuracy is needed for many measurements.

SUMMARY OF THE INVENTION

The present invention is an improvement over the technique developed by Professor Meurens and involves the use of an improved support for the filter paper. In accordance with the invention, the filter paper in which the liquid sample is deposited is supported by a support which contacts the filter only around the periphery of the filter. This arrangement is achieved by a filter holder, which clamps the top and bottom edges of the filter around the periphery between two circular surfaces. The sample is then dried by a stream of hot air directed perpendicularly toward the middle of the filter in an arrangement in which the hot air stream is allowed to pass around the filter as well as through the filter. With the improved filter holder for supporting the filter, more uniform drying of the sample is achieved and greater density of the dried concentrate is provided on the top surface of the filter. As a result, the accuracy of the measurement of the constituents are improved by a factor of about 2.5 and absorption at a maximum absorption wavelength is increased by a factor of about 2 showing that the density of the dried concentrate on the top surface of the filter has been approximately doubled. It is believed that the improved accuracy is achieved because the filter is not contacted by the support structure except where the edges of the filter are clamped between opposing surfaces. Leaving the middle area of the filter free from any solid surface contact eliminates the interference with uniform drying that such contact causes. Also, the lack of any solid contact beneath the middle of the filter promotes a greater migration of the sample to the top surface during drying thus achieving a greater concentration of the dried sample on the top surface.

DESCRIPTION OF A PREFERRED EMBODIMENT

Figure 1:
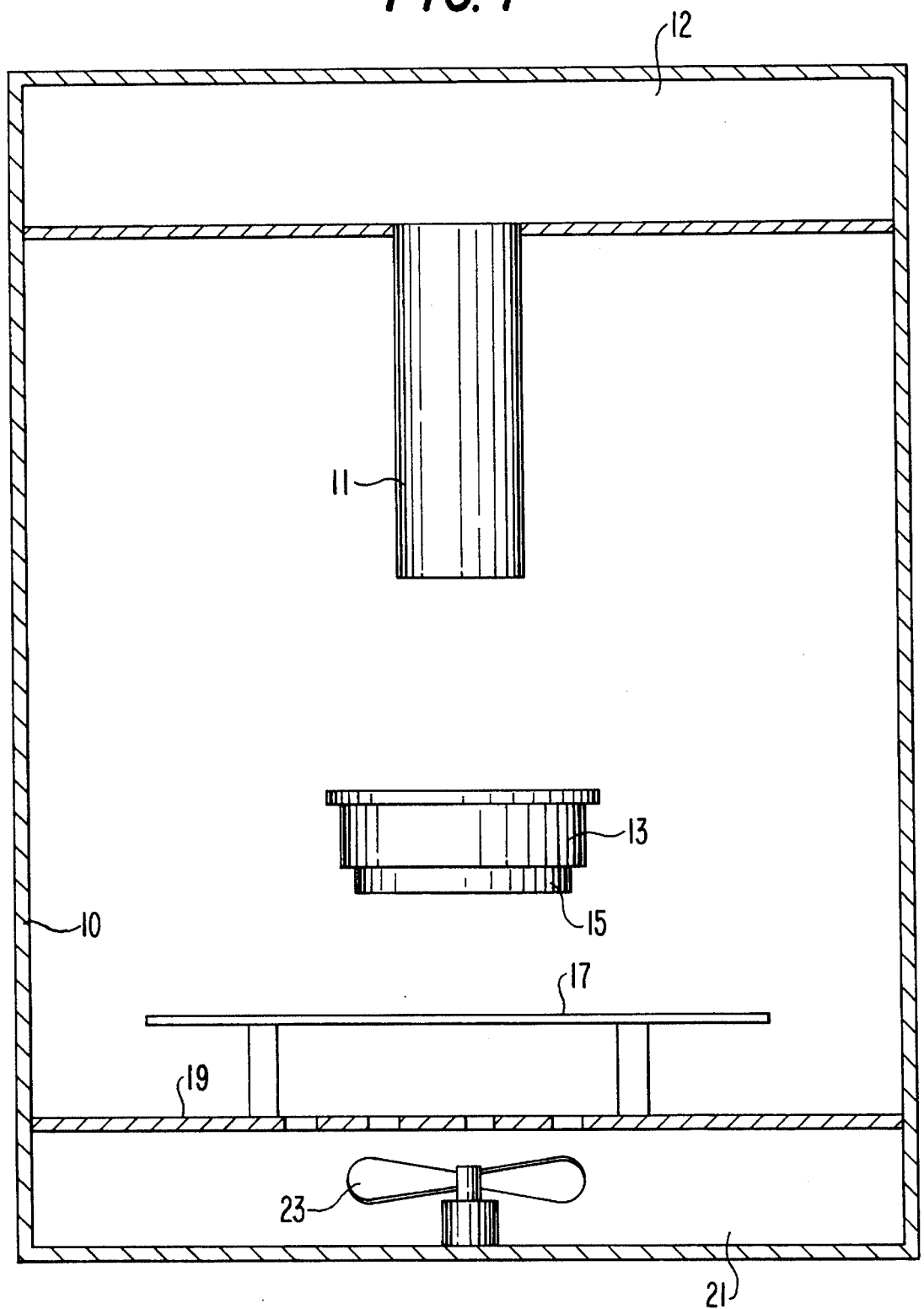
FIG. 1 is a sectional view in elevation schematically illustrating the drying apparatus of the invention.
Figure 3:
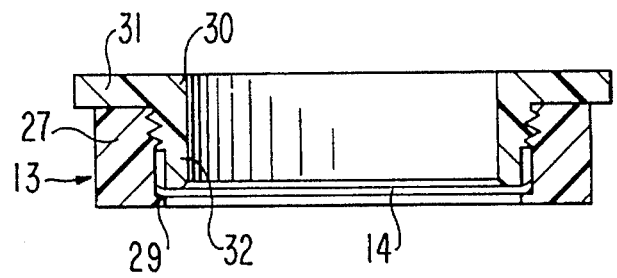
FIG. 3 is an axial sectional view of the filter holder employed in the apparatus shown in FIG. 1.

As schematically shown in FIG. 1, the apparatus of the present invention comprises a housing 10 containing a cylindrical heating tube 11 which connects to an upper manifold 12 open to the atmosphere. Spaced below and aligned with the heating tube 11 is the filter holder 13 which is positioned on a circular support 15. The support 15 is provided with a circular aperture aligned with an aperture in the filter holder in which a filter 14 is mounted as shown in FIG. 3. Spaced below the support 15 is a circular baffle 17 which is supported above a perforated wall 19 defining the upper side of an exhaust fan chamber 21. Within the exhaust fan chamber 21 is an exhaust fan 23 which will operate to draw air from the upper manifold 12 through the heating tube 11, then around and through the filter 14 supported in the filter holder 13. The air then passes around the edges of the baffle 17, through the perforated wall 19 and out through the exhaust chamber 21. As the air passes through the heating tube 11, it will be heated to a temperature between 80° C. and 140° C. and then will be directed at the filter perpendicularly by the tube 11.

Figure 2:
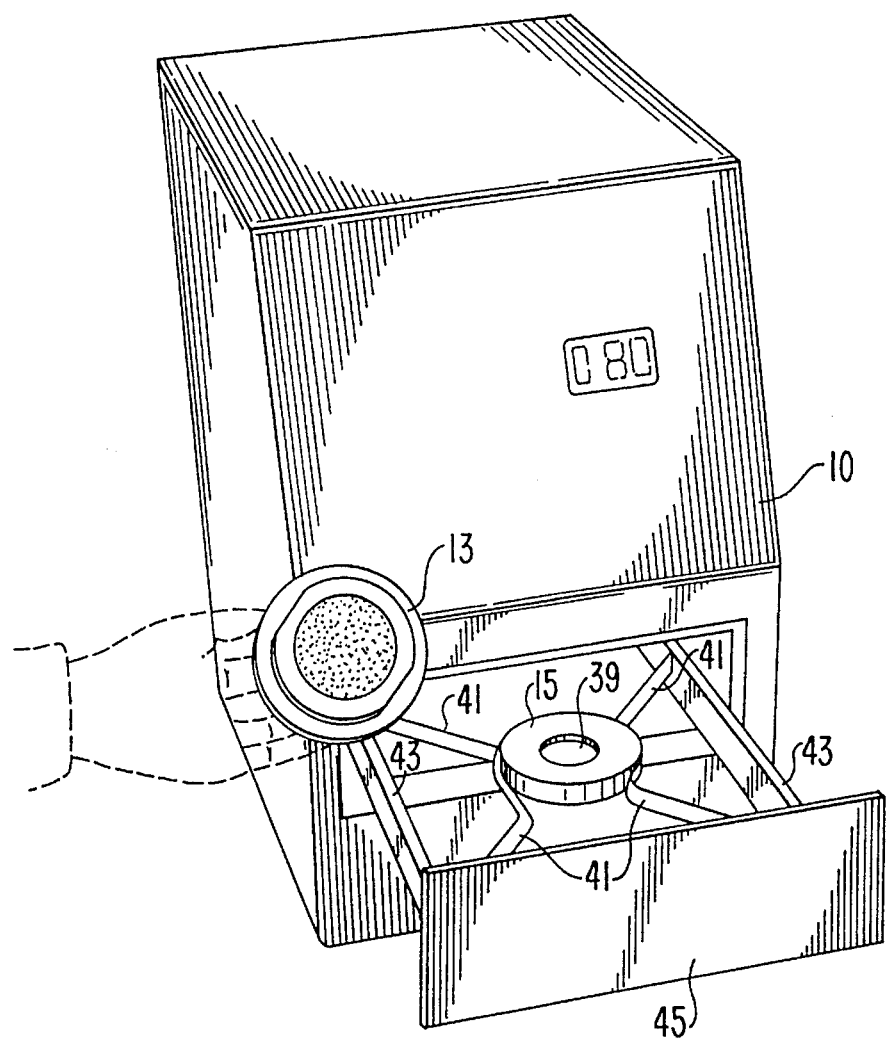
FIG. 2 is a perspective view of the apparatus of FIG. 1 showing the structure of the filter holder support.

As shown in FIG. 2, the filter support 15 comprises a circular plate provided with an aperture 39 in the middle thereof which is aligned with the circular filter when the filter holder 13 is supported on the support 15. The circular plate of the support 15 is supported by four arms 41 on sidewalls 43 of a bottomless drawer 45 which can be slid in and out of the housing 10 of the apparatus to facilitate positioning the filter holder on the support 15.

As shown in FIG. 3, the filter holder comprises a female hollow cylindrical member 27 provided with threads on its inner surface and having an inwardly directed flange 29 at the bottom edge thereof. A male cylindrical member 30 is provided with threads on its outer surface which mate with the threads on the female member 27. The male member 30 is provided with an upper flange 31 which engages the top of the female member 27 when the male member is screwed fully into the female member. The male member 30 is also provided with a cylindrical extension 32 which engages the top of the inwardly directed flange 29 to sandwich the circular glass fiber filter paper 14 between the flange 29 and the cylindrical extension 32 and clamp around the peripheral edge of the filter paper 14.

To carry out the analysis procedure using the apparatus of FIG. 1, the filter paper 14 is clamped in the filter holder 13. The liquid sample to be analyzed is then deposited on filter paper 14. The filter comprises a piece of circular glass fiber filter paper which is available from Aldrich Chemical Co., Inc. of Milwaukee, Wis. The filter holder is then positioned on the support 15 with the drawer pulled out. The drawer is then pushed in the housing to position the filter holder with the filter paper directly below the heating tube. The fan and the heating tube are then energized for a period of three minutes to dry the sample deposited in the filter paper. The fan causes heated air to flow around and through the filter paper with the deposited sample for a period of about three minutes. In this period of time, the sample will be substantially completely dried. Because the top surface of the filter paper will dry first, the sample migrates toward the top surface as the drying takes place increasing the concentration of the dried sample on the top surface. The dried sample on the filter paper is then subject to spectroanalysis in an instrument such as described in copending application Ser. No. 07/294,679, now U.S. Pat. No. 4,969,739 to analyze the composition of the dried concentrate. Application Ser. No. 07/294,679 was filed Jan. 9, 1989, and was invented by Philip A. McGee.

With the arrangement and procedure as described above, the sample on the filter paper can then be dried over the surface of the filter paper with a high degree of uniformity and an increased concentration of the dried sample on the top surface of the filter is obtained. As a result, the constituents in the liquid sample contained in the dried sample on the filter paper can be measured with a high degree of accuracy unachieveable with the systems of the prior art.

The above description is of a preferred embodiment of the invention and modification of the invention may be made thereto without departing from the spirit and scope of the invention which is defined in the appended claims.

We claim:

1. In an apparatus for drying concentrate in filter paper for purposes of analyzing a liquid sample comprising means to generate a heated gas stream, a sheet of porous paper, and holder means to support said sheet of porous paper in the path of said heated gas stream, the improvement wherein said holder means comprises filter holder means to clamp the edges of said sheet of said porous paper between opposed surfaces around the periphery of said porous paper and wherein said apparatus further comprises means for causing said heated gas stream to flow through said sheet of porous paper and around said sheet of porous paper.

2. An apparatus as recited in claim 1, wherein said filter holder means comprises an annular female internally threaded member defining one of said opposed surfaces and an annular external male threaded member adapted to screw into said female member and defining the other one of said opposed surfaces, whereby said sheet of porous paper is clamped between said male and female members.

3. An apparatus as recited in claim 2, wherein said annular female internally threaded member has an inwardly directed flange underlying the periphery of said sheet of said porous paper, and said annular external male threaded member terminates in a lower surface positioned at or above said inwardly directed flange.

4. An apparatus as recited in claim 1, wherein a baffle plate is positioned in the path of said heated gas stream downstream from said filter holder means.

5. An apparatus as recited in claim 1, further comprising a housing enclosing said means to generate said heated gas stream and said filter holder means, said holder means comprising an apertured plate and a holder supported on said plate, said holder defining said opposed surfaces, and a drawer in said housing slidable between extended and enclosed positions supporting said apertured plate, said apertured plate and said holder being positioned in said heated stream when said drawer is in said closed position.

* * * * *